(12) United States Patent
Kosa et al.

(10) Patent No.: US 10,376,261 B2
(45) Date of Patent: Aug. 13, 2019

(54) ANCHORING SUTURE

(75) Inventors: Timothy D. Kosa, Hamden, CT (US); Nicholas Maiorino, Branford, CT (US); Megan Stopek, Yalesville, CT (US)

(73) Assignee: Covidien LP, Mansfield, MA (US)

( * ) Notice: Subject to any disclaimer, the term of this patent is extended or adjusted under 35 U.S.C. 154(b) by 1905 days.

(21) Appl. No.: 12/362,002

(22) Filed: Jan. 29, 2009

(65) Prior Publication Data

US 2009/0248070 A1 Oct. 1, 2009

Related U.S. Application Data

(60) Provisional application No. 61/041,302, filed on Apr. 1, 2008.

(51) Int. Cl.
| | | |
|---|---|---|
| *A61B 17/06* | (2006.01) | |
| *A61B 17/04* | (2006.01) | |
| *A61B 17/00* | (2006.01) | |

(52) U.S. Cl.
CPC .... *A61B 17/06166* (2013.01); *A61B 17/0401* (2013.01); *A61B 17/0469* (2013.01); *A61B 2017/00792* (2013.01); *A61B 2017/00893* (2013.01); *A61B 2017/06028* (2013.01); *A61B 2017/06176* (2013.01)

(58) Field of Classification Search
CPC .... A61B 17/06166; A61B 2017/06176; A61B 2017/06052; A61B 2017/06057; A61B 17/06
USPC ......................................... 606/151, 224–232
See application file for complete search history.

(56) References Cited

U.S. PATENT DOCUMENTS

| | | | | |
|---|---|---|---|---|
| 3,123,077 A | * | 3/1964 | Alcamo | A61B 17/06166 24/30.5 R |
| 3,657,056 A | | 4/1972 | Winston et al. | |
| 3,922,455 A | * | 11/1975 | Brumlik | A44B 18/0015 24/449 |
| 4,024,871 A | | 5/1977 | Stephenson | |
| 4,950,285 A | * | 8/1990 | Wilk | A61B 17/06 24/16 PB |
| 5,002,562 A | * | 3/1991 | Oberlander | A61B 17/064 411/457 |
| 5,019,093 A | | 5/1991 | Kaplan et al. | |
| 5,059,213 A | | 10/1991 | Chesterfield et al. | |
| 5,123,913 A | * | 6/1992 | Wilk | A61B 17/06 24/16 PB |
| 5,133,738 A | | 7/1992 | Korthoff et al. | |

(Continued)

FOREIGN PATENT DOCUMENTS

| | | |
|---|---|---|
| EP | 0494636 A | 7/1992 |
| EP | 0499048 A1 | 8/1992 |

(Continued)

OTHER PUBLICATIONS

European Search Report for EP 09251034 6-1265 date of completion is May 26, 2009 (3 pages).

(Continued)

*Primary Examiner* — Dianne Dornbusch

(57) ABSTRACT

A medical device having an elongate body having a proximal portion and a distal portion, the proximal portion of the elongate body terminating in a free end; the distal portion of the elongate body terminating in a loop. The loop further includes a first plurality of anchors disposed along a surface of the loop.

27 Claims, 3 Drawing Sheets

3A

(56) References Cited

U.S. PATENT DOCUMENTS

| | | | |
|---|---|---|---|
| 5,181,923 A | 1/1993 | Chesterfield et al. | |
| 5,226,912 A | 7/1993 | Kaplan et al. | |
| 5,236,563 A | 8/1993 | Loh | |
| 5,259,846 A * | 11/1993 | Granger | A61B 17/06 606/223 |
| 5,261,886 A | 11/1993 | Chesterfield et al. | |
| 5,269,783 A * | 12/1993 | Sander | A61B 17/06 606/148 |
| 5,306,289 A | 4/1994 | Kaplan et al. | |
| 5,312,436 A * | 5/1994 | Coffey | A61B 17/0469 606/224 |
| 5,318,575 A | 6/1994 | Chesterfield et al. | |
| 5,342,376 A | 8/1994 | Ruff | |
| 5,370,031 A | 12/1994 | Koyfman et al. | |
| 5,383,387 A | 1/1995 | Chesterfield et al. | |
| 5,383,883 A | 1/1995 | Wilk et al. | |
| 5,403,346 A * | 4/1995 | Loeser | A61B 17/06 606/228 |
| 5,417,700 A | 5/1995 | Egan | |
| 5,569,302 A | 10/1996 | Proto et al. | |
| 5,662,682 A | 9/1997 | Chesterfield et al. | |
| 5,667,528 A | 9/1997 | Collligan | |
| 5,683,417 A * | 11/1997 | Cooper | A61B 17/04 606/223 |
| 5,814,056 A | 9/1998 | Prosst et al. | |
| 5,830,234 A | 11/1998 | Wojciechowicz et al. | |
| 5,893,880 A | 4/1999 | Egan et al. | |
| 5,931,855 A | 8/1999 | Buncke | |
| 5,964,765 A * | 10/1999 | Fenton, Jr. | A61B 17/0487 606/103 |
| 5,968,077 A * | 10/1999 | Wojciechowicz | 606/228 |
| 6,063,105 A | 5/2000 | Totakura | |
| 6,106,505 A | 8/2000 | Modak et al. | |
| 6,143,352 A | 11/2000 | Clark et al. | |
| 6,165,202 A | 12/2000 | Kokish et al. | |
| 6,174,324 B1 | 1/2001 | Egan et al. | |
| 6,203,564 B1 | 3/2001 | Hutton et al. | |
| 6,217,591 B1 | 4/2001 | Egan et al. | |
| 6,235,869 B1 | 5/2001 | Roby et al. | |
| 6,241,747 B1 | 6/2001 | Ruff | |
| 6,286,746 B1 | 9/2001 | Egan et al. | |
| 6,296,659 B1 * | 10/2001 | Foerster | A61B 17/0469 606/224 |
| 6,488,690 B1 | 12/2002 | Morris et al. | |
| 6,506,197 B1 | 1/2003 | Rollero et al. | |
| 6,534,693 B2 * | 3/2003 | Fischell et al. | 602/43 |
| 6,562,051 B1 | 5/2003 | Bolduc et al. | |
| 6,599,310 B2 * | 7/2003 | Leung | A61B 17/04 606/228 |
| 6,620,846 B1 | 9/2003 | Jonn et al. | |
| 6,692,499 B2 | 2/2004 | Tormala et al. | |
| 6,773,450 B2 | 8/2004 | Leung et al. | |
| 6,923,824 B2 | 8/2005 | Morgan et al. | |
| 7,090,111 B2 | 8/2006 | Egan et al. | |
| 7,744,611 B2 * | 6/2010 | Nguyen | A61B 17/0469 606/151 |
| 8,932,328 B2 * | 1/2015 | Megaro | A61B 17/06109 606/148 |
| 9,034,011 B2 * | 5/2015 | Kirsch | A61B 17/0401 606/228 |
| 2002/0077661 A1 | 6/2002 | Saadat | |
| 2002/0177876 A1 | 11/2002 | Roby et al. | |
| 2003/0074023 A1 | 4/2003 | Kaplan et al. | |
| 2003/0078603 A1 * | 4/2003 | Schaller | A61B 17/0469 606/151 |
| 2003/0097148 A1 | 5/2003 | Valimaa et al. | |
| 2003/0149447 A1 * | 8/2003 | Morency | A61B 17/06166 606/228 |
| 2004/0010275 A1 | 1/2004 | Jacobs et al. | |
| 2004/0030354 A1 | 2/2004 | Leung et al. | |
| 2004/0060409 A1 | 4/2004 | Leung et al. | |
| 2004/0060410 A1 | 4/2004 | Leung et al. | |
| 2004/0087974 A1 | 5/2004 | Bittar | |
| 2004/0088003 A1 | 5/2004 | Leung et al. | |
| 2004/0122451 A1 | 6/2004 | Wood | |
| 2004/0153125 A1 | 8/2004 | Roby | |
| 2004/0162580 A1 | 8/2004 | Hain | |
| 2005/0033367 A1 | 2/2005 | Leung et al. | |
| 2005/0049635 A1 | 3/2005 | Leiboff | |
| 2005/0049636 A1 * | 3/2005 | Leiboff | A61B 17/0401 606/213 |
| 2005/0165448 A1 | 7/2005 | Egan et al. | |
| 2005/0209639 A1 | 9/2005 | Gidwani et al. | |
| 2005/0216058 A1 | 9/2005 | Egan et al. | |
| 2005/0240224 A1 * | 10/2005 | Wu | A61B 17/06166 606/228 |
| 2005/0267479 A1 | 12/2005 | Morgan et al. | |
| 2005/0267520 A1 | 12/2005 | Modesitt | |
| 2005/0267531 A1 * | 12/2005 | Ruff | A61B 17/04 606/228 |
| 2005/0267532 A1 * | 12/2005 | Wu | A61B 17/06166 606/228 |
| 2006/0116718 A1 | 6/2006 | Leiboff | |
| 2006/0206096 A1 | 9/2006 | Accisano, III et al. | |
| 2006/0247643 A1 * | 11/2006 | Bhatnagar | A61B 17/0642 606/75 |
| 2007/0005110 A1 | 1/2007 | Collier et al. | |
| 2007/0021780 A1 | 1/2007 | Harrington et al. | |
| 2007/0187861 A1 | 8/2007 | Genova | |
| 2007/0224237 A1 | 9/2007 | Hwang et al. | |
| 2008/0027486 A1 * | 1/2008 | Jones | A61B 17/0469 606/228 |
| 2008/0058869 A1 * | 3/2008 | Stopek | A61B 17/06166 606/228 |
| 2008/0200950 A1 * | 8/2008 | Wohlert | A61B 17/064 606/221 |
| 2008/0281357 A1 * | 11/2008 | Sung | A61B 17/06166 606/232 |
| 2009/0099597 A1 * | 4/2009 | Isse | A61B 17/06166 606/228 |
| 2009/0248070 A1 * | 10/2009 | Kosa | A61B 17/06166 606/232 |
| 2009/0306681 A1 * | 12/2009 | Del Nido | A61B 17/0401 606/139 |
| 2011/0319932 A1 * | 12/2011 | Avelar | A61B 17/0469 606/228 |

FOREIGN PATENT DOCUMENTS

| | | |
|---|---|---|
| EP | 0 632 999 A | 1/1995 |
| EP | 0 632 999 A1 | 1/1995 |
| EP | 0647452 A1 | 4/1995 |
| EP | 1 669 093 | 6/2006 |
| EP | 1 656 890 B1 | 12/2008 |
| EP | 2 106 752 A1 | 10/2009 |
| EP | 2106752 A1 | 10/2009 |
| JP | 2008-253791 A | 10/2008 |
| JP | 2009247890 A | 10/2009 |
| WO | WO 91/07916 A1 | 6/1991 |
| WO | WO 97/08238 | 3/1997 |
| WO | WO 98/00065 | 1/1998 |
| WO | 9852473 | 11/1998 |
| WO | WO 99/52451 A | 10/1999 |
| WO | WO 00/57933 A | 10/2000 |
| WO | WO 01/52751 A | 7/2001 |
| WO | 03001979 | 1/2003 |
| WO | 2004014236 | 2/2004 |
| WO | 2004030520 | 4/2004 |
| WO | 2004030704 | 4/2004 |
| WO | 2004030705 | 4/2004 |
| WO | WO 2004/045663 A2 | 6/2004 |
| WO | WO 2004/066927 A2 | 8/2004 |
| WO | WO 2005/080495 | 1/2005 |
| WO | 2006079469 | 8/2006 |
| WO | WO 2007/133103 A | 11/2007 |
| WO | WO 2007/133103 A1 | 11/2007 |
| WO | WO 2008/042909 | 4/2008 |

(56) References Cited

FOREIGN PATENT DOCUMENTS

WO    WO 2008/107919 A    9/2008
WO    WO 2008/141034 A1    11/2008

OTHER PUBLICATIONS

European Search Report for Appln. No. 09251035.3 dated Jun. 3, 2009.
Partial European Search Report from application No. 07 25 4341 dated Apr. 20, 2009.
JLT1204-211-229(175):R.R. Szarmach et al., Journal of Long-Term Effects of Medical Implants, "An Innovative Surgical Suture and Needle . . ." 12(4), pp. 211-229(2002).
George Odian, "Principles of Polymerization," III Edition, pp. 569-573 (1991).
International Search Report from Appln. No. EP 06 012688 dated Aug. 1, 2007.
European Search Report from Appln. No. EP 07 253438 dated Feb. 1, 2008.
European Search Report for Appln. No. 09250460 dated Jun. 2, 2009.
European Search Report from application No. 07 25 4703 dated Feb. 10, 2009.
U.S. Appl. No. 60/994,173, filed Sep. 17, 2007, Maiorino et al.
European Search Report for EP 10177651.6-1526 date of completion is Dec. 14, 2010 (3 pages).
European Search Report for EP 12169125.7-1269 date of completion is Jun. 22, 2012 (5 pages).
European Search Report for EP 12166183.9-1269 date of completion is Jul. 5, 2012 (8 pages).
European Search Report for EP 11250537.1269 date of completion is Aug. 8, 2011 (3 pages).
Japanese Office Action dated Jun. 2, 2015 in corresponding Japanese Patent Application No. 2011-103867.
EP Examination Report dated Jun. 13, 2017, issued in EP Application No. 12169125.

* cited by examiner

ANCHORING SUTURE

CROSS-REFERENCE TO RELATED APPLICATIONS

This application claims the benefit of and priority to U.S. Provisional Patent Application No. 61/041,3028, filed Aug. 1, 2008, the entire disclosure of which is incorporated by reference herein.

BACKGROUND

1. Technical Field

The present disclosure relates generally to the field of surgical devices, and more particularly to devices such as sutures which include a distal loop having anchors disposed along a surface.

2. Background of Related Art

Surgical sutures have been successfully used for various types of medical procedures, including tissue and would closure. Surgical sutures typically have a needle attached at one end. As the needle penetrates tissue, the suture enters, passes through, and exits tissue, at which point knots may be used to secure the tissue or wound.

Additionally, sutures typically employ a knot at the distal end to secure the suture end in tissue, permitting movement of the free end through tissue. Knot tying adds time to a procedure and may result in additional bulk material being left at the wound site. Improvements in the field are desired.

SUMMARY

The present disclosure relates to a medical device having an elongate body having a proximal portion and a distal portion; the proximal portion terminating in a free end and the distal portion terminating in a loop. The loop also includes a first plurality on anchors disposed along a surface of the loop. The elongate body may also include a second plurality of anchors, wherein the first plurality of anchors is different from the second plurality of anchors. In preferred embodiments, the first plurality of anchors is positioned adjacent to a transition area; the transition area being defined by an intersection of the elongate body and the loop. As described herein, the first plurality of anchors may limit movement of the loop through tissue.

Additionally, the loop portion of the medical device may be formed via ultrasonic energy, welding, cutting, gluing, heating, forming or molding. In certain embodiments the proximal portion of loops formed via ultrasonic energy has a second plurality of anchors, wherein the first plurality of anchors extends in a first direction and the second plurality of anchors extend in a second, different direction. In alternate embodiments, the loop may be created using adhesives, glues or sealants.

In some embodiments one or more of the anchors of either or both the first plurality of anchors or the second plurality of anchors may define at least one compound barb. The compound barb defines an inner surface having a first portion and a second portion wherein the first portion includes a first orientation relative to a longitudinal axis of the elongate body, the second portion is disposed at a second orientation relative to the longitudinal axis, and optionally a third portion of the inner surface is disposed at a third orientation relative to the longitudinal axis. In certain embodiments, the first, second and third orientations are different.

Absorbable, non-absorbable and combinations of absorbable and non-absorbable materials may be used to make medical devices of the present disclosure. Absorbable materials may include lactide, glycolide, caprolactone, valerolactone, trimethylene carbonate, 1,4-dioxanone, δ-valerolactone, ε-caprolactone, 1,4-dioxepan-2-one, 1,5-dioxepan-2-one, collagen, gut, polymer drugs, ethylene glycol, ethylene oxide, esteramides, γ-hydroxyvalerate, β-hydroxypropionate, alpha-hydroxy acid, and β-hydroxybuterate, collagen, cellulose, gut, and copolymers thereof. Non-absorbable materials may include silk, cotton, rubber, nylon, polypropylene, polyethylene, ultrahigh molecular weight polyethylene (UHMWPE), polyethylene terephthalate (PET), and polyesters and copolymers thereof.

In certain embodiments, medical devices of the enclosed disclosure include sutures, clips, fasteners, wound dressings, meshes, bandages, drug delivery devices, anastomotic rings, stents, grafts, catheter systems, tissue scaffolds, buttresses, pledgets, soft tissue repair and augmentation devices, tapes and ribbons. In other embodiments, the medical device further includes a medicinal agent.

The enclosed disclosure also includes a suture comprising an elongate body having a proximal portion and a distal portion wherein the proximal portion of the elongate body has a free end and the distal portion of the elongate body transitions into a loop. The loop also has a first plurality of tissue engaging members located adjacent to the elongate body. In other embodiments, the elongate body further comprises a second plurality of tissue engaging members.

A method for closing body tissue is also disclosed providing the claimed medical device. The method may include the steps of inserting the proximal portion of the medical device through a first section of tissue; advancing the proximal portion of the medical device through a second section of tissue wherein the first plurality of anchors limits movement of the suture loop such that a segment of the loop remains outside a body tissue. This method may further comprise the step of inserting the proximal portion of the medical device through the segment of the loop remaining outside the body tissue.

BRIEF DESCRIPTION OF DRAWINGS

Various preferred embodiments of the sutures are described herein with reference to the drawings, in which.

DETAILED DESCRIPTION OF EMBODIMENTS

Figure 1A:
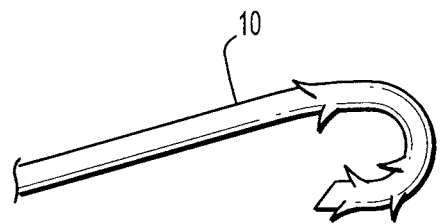
FIGS. 1a-1b are side views illustrating one embodiment of a looped suture.

The present disclosure is directed to a medical device and in preferred embodiments, a suture, herein referred to as an anchoring suture. The anchoring sutures disclosed have an elongate body which connects to a needle at a proximal end and a distal end of the elongate body extends into an anchoring loop. The anchoring loop further includes a plurality of anchors (tissue engaging members). Medical devices of the present disclosure include sutures formed from fibers, filaments, and yarns.

Sutures of the present disclosure may be absorbable or non-absorbable. It should be understood that combinations of filaments made from different materials (e.g. natural and synthetic, or bioabsorbable and non-bioabsorbable materials) may be used to make the present anchoring suture.

Suitable synthetic absorbable materials include polymers such as those made from lactide, glycolide, caprolactone, valerolactone, carbonates (e.g., trimethylene carbonate, tetramethylene carbonate), dioxanones (e.g., 1,4-dioxanone) δ-valerolactone, 1,dioxepanones (e.g., 1,4-dioxepan-2-one and 1,5-dioxepan-2-one), ethylene glycol, ethylene oxide, esteramides, γ-hydroxyvalerate, β-hydroxypropionate, alpha-hydroxy acid, hydroxybuterates, orthoesters, hydroxy alkanoates, tyrosine carbonates, polyimide carbonates, polyimino carbonates such as poly (bisphenol A-iminocarbonate) and poly (hydroquinone-iminocarbonate), and polymer drugs (e.g., polydiflunisol, polyaspirin, and protein therapeutics) and copolymers and combinations thereof. Suitable natural absorbable polymers include collagen, cellulose and gut. In embodiments, glycolide and lactide based polyesters, including copolymers of lactide and glycolide may be used.

Suitable non-absorbable materials which may be used to form the anchoring sutures disclosed herein include non-absorbable natural materials such as cotton, silk, and rubber. Suitable non-absorbable synthetic materials include monomers and polymers derived from materials such as nylons, polyolefins such as polypropylene and polyethylene, ultra high molecular weight polyethylene (UHMWPE), polyamides, polyesters such as poly ethylene terephthalate (PET), polyaryletherketone, polyvinylidene difluoride (PVDF), acrylic, polyamides, aramids, fluropolymers, polybutesters, silicones, and polymer blends, copolymers thereof and combinations with degradable polymers. Polypropylene can also be utilized to form the suture. The polypropylene can be isotactic polypropylene or a mixture of isotactic and syndiotactic or atactic polypropylene. Additionally, non-absorbable synthetic and natural polymers and monomers may be combined with each other and may also be combined with various absorbable polymers and monomers to create fibers and filaments for the present anchored suture.

In certain embodiments, anchoring sutures in whole or part (e.g. anchors) may be constructed using shape memory polymers. Suitable polymers used to prepare hard and soft segments of shape memory polymers include polycaprolactone, dioxanone, lactide, glycolide, polyacrylates, polyamides, polysiloxanes, polyurethanes, polyether amides, polyurethane/ureas, polyether esters, and urethane/butadiene copolymers and combinations thereof.

In some embodiments, the sutures may include metals (e.g. steel and degradable magnesium), metal alloys or the like.

As used herein, the terms "fibers", "filaments" and "yarns" each may be used to construct in whole or in part anchoring sutures. The term "fibers," in this context, are generally used to designate natural or synthetic structures that have a length approximately 3 orders of magnitude greater than their diameter or width. The term "filaments" are typically used to describe "fibers" of indefinite or extreme length, and "yarns" as a generic term for a continuous strand of twisted or untwisted "fibers" or "filaments" in a form suitable for knitting, weaving, braiding or otherwise intertwining.

Sutures of the present disclosure may be monofilament or multifilament (e.g. braided). Methods for making sutures from these suitable materials are within the purview of those skilled in the art (e.g. extrusion and molding). The filaments may be combined to create a multifilament suture using any technique within the purview of one skilled in the art such as commingling, twisting, braiding, weaving, entangling, and knitting. For example, filaments may simply be combined to form a yarn or they may be braided. In another example, filaments may be combined to form a yarn and then those multifilament yarns may be braided. Those skilled in the art reading this disclosure will envision other ways in which filaments may be combined. Fibers may also be combined to produce a non-woven multifilament large diameter suture. In certain embodiments, a multifilament structure useful in forming an anchoring suture according to the present disclosure may be produced by braiding. The braiding can be done by any method within the purview of those skilled in the art. For example, braid constructions for sutures and other medical devices are described in U.S. Pat. Nos. 5,019,093; 5,059,213; 5,133,738; 5,181,923; 5,226,912; 5,261,886; 5,306,289; 5,318,575; 5,370,031; 5,383,387; 5,662,682; 5,667,528; and 6,203,564; the entire disclosures of each of which are incorporated by reference herein. Furthermore, the anchoring suture may include portions which are monofilament and portions which are multifilament. In some embodiments, the proximal end of the elongate body may be a multifilament and the looped portion (loop portion described below) may be a monofilament.

Additionally, the suture may include biologically acceptable additives such as plasticizers, antioxidants, dyes, dilutants, bioactive agents and combinations thereof, which can be coated on the filaments or fibers, or impregnated into the fibers or filaments (e.g. during compounding or extrusion) used to form the anchoring suture of the present disclosure.

Various compositions and materials may also be applied to the anchoring sutures or included in the filaments or fibers to improve mechanical properties such as handling and knot strength or to deliver medicinal agents. Suitable coating materials include any materials conventionally applied to sutures. For example, suitable materials include fatty acid esters which may be combined with the metal salt of a fatty acid in the coating composition. Such esters include, for example, calcium stearate, stearoyl lactylate esters, palmityl lactylate esters, oleyl lactylate esters such as calcium, magnesium, aluminum, barium, or zinc stearoyl lactylate, calcium, magnesium, aluminum, barium, or zinc palmityl lactylate; calcium, magnesium, aluminum, barium, or zinc oleyl lactylate; with calcium stearate and calcium stearoyl-2-lactylate (such as the calcium stearoyl-2-lactylate commercially available under the trade name VERV from American Ingredients Co., Kansas City, Mo.) being preferred. When desirable, the fatty acid ester may be combined with a solvent. Suitable solvents include polar and non-polar solvents including but not limited to alcohols (e.g., methanol, ethanol, propanol), chlorinated hydrocarbons (such as methylene chloride, chloroform, 1,2-dichloro-ethane), and aliphatic hydrocarbons such as hexane, heptene, ethyl acetate.

In embodiments, the anchoring suture may be combined with and/or coated with suitable materials including polyalkylene oxides such as polyethylene oxide, polypropylene oxide, polyethylene glycol (PEG), polypropylene glycol, copolymers thereof, and the like, including those having acrylate groups such as acrylate PEGs, and acrylate PEG/PPG copolymers. Such combinations may include blends or copolymers with polyalkylene oxide oligomers or polymers or other non-toxic surfactants. The resulting composition may possess antimicrobial properties due to the presence of the copolymers described above. In other embodiments, the sutures may be combined with silicone acrylates. Coatings may be applied to the individual filaments or the anchoring suture at any time prior to sterilization techniques. Coatings can be applied to the filaments using any technique within the purview of those skilled in the art.

Additionally, the anchoring suture may incorporate various pharmaceuticals and medicinal agents. Medicinal agents and drugs may be applied to the sutures and/or construct materials by methods within the purview of those skilled in the art, including but not limited to dipping, spraying, brushing, vapor deposition, coextrusion, capillary wicking, film casting, molding and the like. Additionally, solvents may be used to incorporate various agents into the anchoring suture. Suitable solvent include those listed above.

Medicinal agents which may be incorporated into the suture include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, and combinations thereof.

Agents may be incorporated into a coating using solvents or mixed with various monomers or polymers and applied to anchoring suture. Additional suitable medicinal agents which may be used include colorants, dyes, preservatives, protein and peptide preparations, protein therapeutics, polysaccharides such as hyaluronic acid, lectins, lipids, probiotics, antibiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, brominated or halogenated furanones, and the like. In embodiments, polymer drugs, i.e., polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS), and the like may be utilized and combinations thereof.

The anchoring suture of the present disclosure can additionally contain suitable medicinal agents such as viruses and cells, peptides, polypeptides and proteins, analogs, muteins, and active fragments thereof, such as immunoglobulins, antibodies (monoclonal and polyclonal), cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids, such as antisense molecules, DNA, RNA, oligonucleotides, polynucleotides and ribozymes and combinations thereof.

Methods for combining these medicinal agents with compositions of the present disclosure are within the purview of those skilled in the art and include, but are not limited to mixing, blending, dipping, spraying, wicking, solvent evaporating and the like.

Sutures of the present disclosure include an elongate body, having both distal and proximal portions, the distal portion of which transitions from the elongate body to an anchoring loop. Methods for creating anchoring loops are within the purview of those skilled in the art and include but are not limited to welding, ultrasonic energy, cutting, molding and gluing. In preferred embodiments to be described later, the anchoring loop includes barbs along a surface.

Figure 1B:
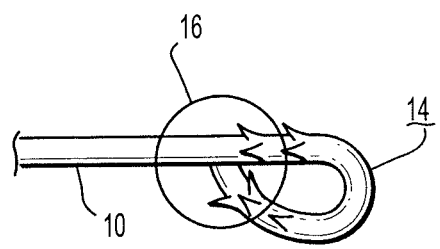
Figure 2A:
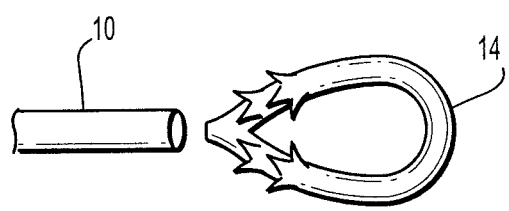
FIGS. 2a-2b are side views illustrating another embodiment of a looped suture.
Figure 2B:
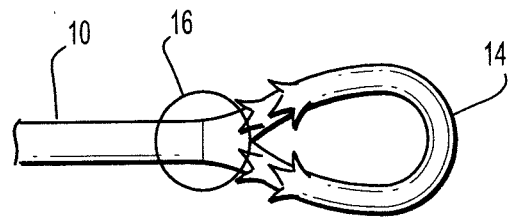

Adjuncts to making loops, such as adhesives and glues, may also be employed in the anchoring suture. In some embodiments (FIGS. 1a, 1b), the distal portion of suture may be folded and fixed to elongate body using adhesives and glues. In alternate embodiments, as shown in FIGS. 2a and 2b, loop portion may initially be a separate component which connects to an elongate body and optionally glued in place. It should be understood that embodiments and methods described in FIGS. 1 and 2 can be used to create any of the anchoring suture embodiments described herein (FIGS. 3-6). Suitable materials such as absorbable and non-absorbable materials include, but not limited to cyanoacrylates, isocyanates, polyurethanes, polyamines, polyamides, polyacrylates, polymethacrylates, silicones, carbonates, and other synthetic monomers and polymers and combinations thereof.

Adhesives such as cyanoacrylates can be employed in creating sutures of the present disclosure. Suitable cyanoacrylates include materials derived from methyl cyanoacrylate, ethyl cyanoacrylate, butyl cyanoacrylate, octyl cyanoacrylate, isobutyl cyanoacrylate, and methoxypropyl cyanoacrylate and combinations thereof and the like.

The anchoring loop further includes anchors disposed along a surface. Anchors can be created on the anchoring suture using any technique, including but not limited to lasers, molding, knives, blades, stamping, and other cutting means within the purview of those skilled in the art. Ultrasonic energy can also be used to create barbs or anchors as described in U.S. Patent Application No. 60/994,173 filed on Sep. 17, 2007 entitled "Method of Forming Barbs on a Suture" the entire disclosures of which are incorporated by reference herein.

Figure 3:
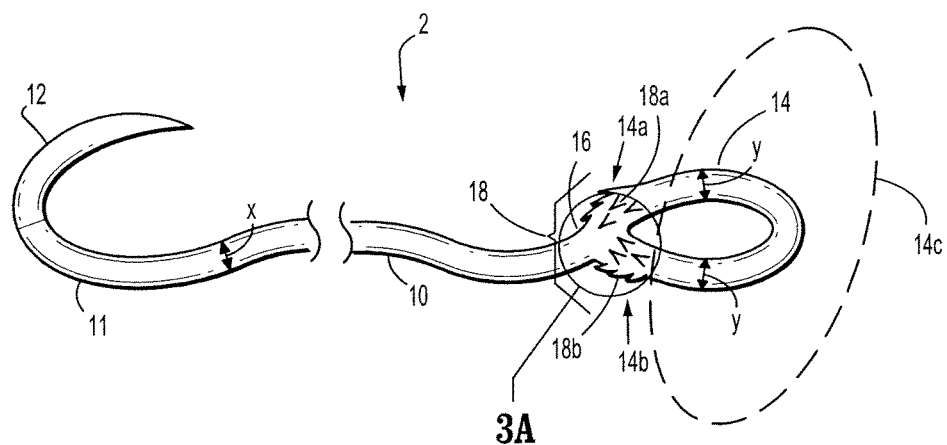
FIG. 3 is a side view illustrating one embodiment of an anchoring suture including barbs.

In some embodiments, anchoring sutures of the present disclosure include loops which are integral to an elongate body, as shown in FIGS. 1 and 3. Sutures with integral loops may be defined as having one structure or component in which the elongate body is continuous with the loop. For example, FIG. 1 shows an elongate body 10 in which the distal end is folded or "looped" to create a loop 14 at the distal end of the medical device. The suture as shown in FIGS. 1 and 2 further includes transition area 16 and anchors 18 which will be described in further detail below. An anchoring suture may also contain an integral loop as shown in FIG. 3, wherein the loop portion may be molded. In alternate embodiments, such as FIG. 2, anchoring sutures may comprise two components which are fixed or fitted together in a fashion as to create the anchoring suture. For example, the elongate body 10 may include a female component while the loop 14 may include a male component and the two components may be fitted together to create a final product. One skilled in the art can envision other manufacturing processes in which to create integral loops and medical devices with integral and non-integral loops.

Figure 3A:
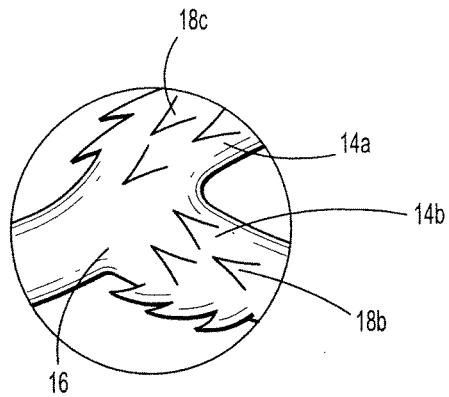
FIG. 3A is a enlarged view of the area of detail designated in FIG. 3.

Another embodiment of the anchoring suture of the present disclosure is shown in FIG. 3 and is designated generally by reference numeral 2. Suture 2 has an elongate body 10, a proximal portion of elongate body 10 terminating in a free end 11, and a distal portion of the elongate body 10 which transitions into or terminates in a loop 14. As shown in FIG. 2, the free end 11 further comprises a needle 12. The elongate body 10 has a diameter "x" and in preferred embodiments, the elongate body 10 is generally elliptical in transverse cross-section. The distal end of elongate body 10 extends into a loop 14, bifurcating at transition area 16 (FIGS. 3 and 3a). Loop 14 includes two branches 14a and 14b, which may be identical in shape and cross-sectional area, to both each other and elongate body 10. In preferred embodiments, sections 14a and 14b are generally elliptical in shape and cross-sectional area, although other shapes are envisioned such as circular, oval, square, and rectangular. In the embodiment shown in FIG. 3, the loop 14 may be integral with the elongate body 10 of the suture 2. In alternate embodiments, the loop 14 may be a separate component prior to assembly (FIGS. 1 and 2), and during assembly the loop 14 may be attached to the elongate body 10. The loop 14 has a generally arcuate surface, and each branch (14a and 14b) has an independent diameter "y", of which 14a and 14b may be of similar or different diameters.

Furthermore, anchoring suture of FIG. 3 includes a first plurality of anchors 18 disposed along a surface of the loop 14. Anchors 18a are disposed along surface of branch 14a and anchors 18b are disposed along branch 14b. Additionally, segment 14c is used to designate loop segment in which anchors are absent. In the illustrated embodiment, anchors 18 are located adjacent transition area 16 of elongate body 10 and anchoring loop 14. Furthermore, the first plurality of anchors 18 is oriented such that movement of the anchoring loop 14 towards the proximal end is limited. As shown in FIG. 3, anchors 18 are oriented towards transition area 16 to prevent movement of anchoring loop 14 through tissue. In embodiments shown, anchors 18 are integral to the anchoring loop 14.

Figure 4:
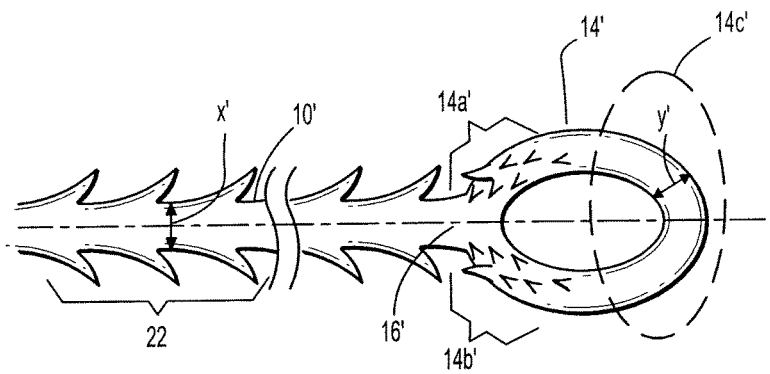
FIG. 4 is a side view illustrating an alternate embodiment of an anchoring suture including barbs.

It will be understood that FIG. 4 is a similar embodiment to FIG. 3 and therefore all numerals and descriptions which are the same in FIG. 3 are designated with the prime mark and the differences will be described below. FIG. 4 shows an alternate embodiment of an anchoring suture 2' in which a second plurality of anchors 22 is disposed along the elongate body 10'. The second plurality of anchors 22 extends in the second direction which is different from a first direction of the first plurality of anchors. In the embodiment shown, the first plurality of anchors 18' are disposed along a loop surface and extend in the first direction, generally towards transition area 16' of the anchoring suture 2'. The second plurality of anchors 22 extend in a second direction, towards the loop 14', with respect to longitudinal axis A of the elongate body 10. As shown in FIG. 4. the first plurality of anchors 18' and the second plurality of anchors 22 extend in directions substantially opposite to one another. The second plurality of anchors 22 permits movement of the elongate body 10' in the direction of the leading or proximal end while preventing movement of the elongate body 10' towards the loop end.

Figure 5:
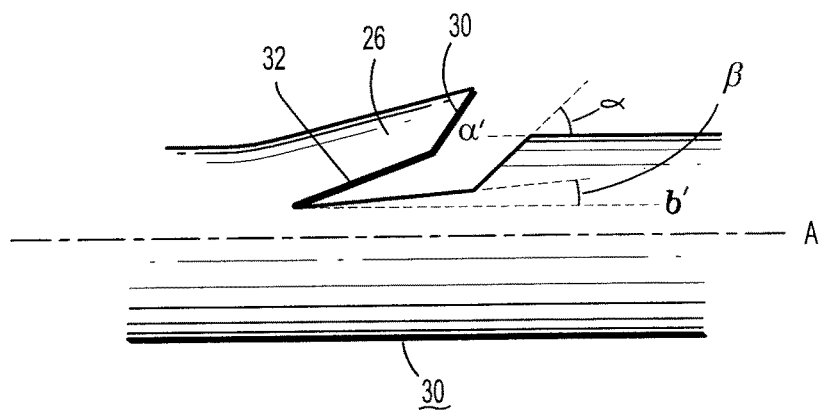
FIG. 5 is an enlarged side view of a barb of an alternate embodiment of an anchoring suture with a compound barb; and, FIGS. 6a-6b is a plan view and a side view of FIG. 4 in tissue with portions of tissue removed.

The anchors can be arranged in any suitable pattern along elongate body and anchoring loop including helical, linear, or randomly spaced with respect to longitudinal axis "A". The number, configuration, spacing and surface area of the anchors can vary depending upon the tissue in which the suture is used, as well as the composition and geometry of the material utilized to form the suture. For example, if the wound closure device is intended to be used in fatty tissue, which is relatively soft, the anchors may be longer and spaced further apart to enable to suture or mesh to grip the soft tissue. The anchors can be arranged in various directions at various angles or a single barb may include more than one angle, such as a compound barb. In the alternate embodiment shown in FIG. 5, anchoring suture 30 includes a compound barb 26 having an inner surface 30 including a first angle $\alpha$, disposed at a first orientation relative to a longitudinal axis "A" of the elongate body and a second angle $\beta$ having a second inner surface 32, disposed at a second orientation relative to a longitudinal axis b of the elongate body. The anchoring suture may optionally include a third orientation (not shown). In the embodiment shown, the first, second and third orientations are each disposed at different angles with respect to the longitudinal axis. In some embodiments, the anchoring suture may include a staggered arrangement of large or small barbs. In other embodiments, an anchoring suture may have a random configuration of both large and small barbs. It will be understood that the embodiment shown in FIG. 5 is similar in most respects to FIGS. 3 and 4, with the only difference being the geometry of the barbs. In alternate embodiments, the above-mentioned compound barb geometry may also be present on the anchoring loop (not shown).

The surface area of the plurality of anchors can also vary. For example, fuller-tipped anchors can be made of varying sizes designed for specific surgical applications. When joining fat and relatively soft tissues, larger anchors may be desired, whereas smaller anchors may be more suitable for collagen-dense tissues. In some embodiments (FIG. 4), a combination of large and small anchors within the same structure may be beneficial, for example when a fiber is used in tissue repair with differing layer structures. Use of the combination of large and small anchors with the same fiber wherein anchor sizes are customized for each tissue layer will ensure maximum holding properties.

As used herein, the term "tissue" includes, but is not limited to, tissues such as skin, fat, fascia, bones, muscles, tendons, ligaments, organs, nerves, and blood vessels. Also used herein, the term "wound" includes, but is not limited to, a surgical incision, cut, laceration or severed tissue in human or animal skin or other human or animal bodily tissue.

Figure 6A:
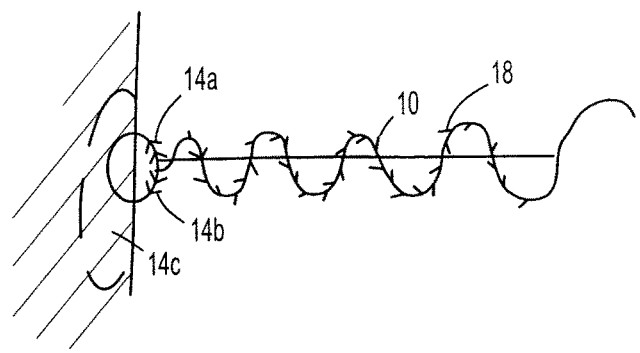
Figure 6B:
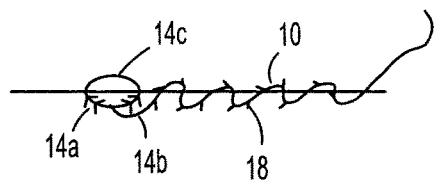

Tissue may be sutured by inserting proximal portion of anchoring suture into tissue at a first section and advancing the proximal portion of the suture through a second section of the tissue, and exiting tissue at an exit point. Suture is pulled through the exit point until the first plurality of anchors on the anchoring loop engages tissue and resists movement in direction of needle advancement, thus preventing further advancement of anchoring loop through tissue. The proximal portion of the suture may optionally be inserted through the segment of the loop remaining outside the body tissue for enhanced fixation. FIGS. 6a and 6b show the embodiment of FIG. 4, where an unanchored loop segment 14c' remains exterior to wound site (or external to skin in dermal closure) due to anchors 18a' and 18b' and lack of anchors on segment 14c'. It should be understood that all embodiments described herein can be used in a similar fashion. Upon exit of tissue, needle and proximal end of suture may be passed through segment of loop 14c' which remains exterior to wound site to secure suture in place. User may then continue suturing wound, entering and exiting tissue until wound site is closed (or implant attached).

In order to facilitate needle attachment to a suture of the present disclosure, conventional tipping agents can be applied to the braid. Two tipped ends of the fiber may be desirable for attaching a needle to each end of the fiber to provide a so-called double armed suture. The needle attachment can be made by any conventional method such as crimping, swaging, etc, as is known within the purview of those skilled in the art. Alternatively, a reduced diameter may be provided at the end of the suture to be inserted into the drilled end of a needle. To provide a reduced diameter, the suture may by machined using any technique within the purview of those skilled in the art, such as cutting, grinding, laser machining or the like.

Anchoring sutures of the present disclosure may be employed in medical devices, drug delivery devices and cell growth substrates. Examples of suitable medical devices and/or surgical devices employing the anchoring sutures may include, but are not limited to meshes, wound dressings, bandages, drug delivery devices, anastomosis rings, stents, grafts, catheter systems, soft tissue repair and augmentation devices, scaffolds, buttresses, lap bands, tapes, anchors, ribbons, orthopedic devices, tissue engineering scaffolds, various cell growth substrates, and other implantable devices. In some embodiments, sutures of the present disclosure may be knitted or woven with other fibers, either absorbable or non-absorbable, to form surgical devices. The anchoring sutures also can be made into meshes or nonwoven materials to form fabrics, such as matted fabrics and felts.

Additionally, the anchoring suture of the present disclosure may be packaged using materials known to those within the purview of those skilled in the art, including foil and various plastics (e.g. polyethylene), which may provide a moisture barrier.

Once the anchoring suture is constructed, it can be sterilized by any means within the purview of those skilled in the art including but not limited to ethylene oxide, electron beam (e-beam), gamma irradiation, autoclaving, and the like.

EXAMPLE 1

Distal end of Maxon™ suture is folded towards elongate body to create a loop, and suture (loop) is then placed in an ultrasonic welding apparatus, where loop is welded closed. Suture is then affixed to an ultrasonic cutting apparatus to create barbs. Elongate body and anchoring loop of anchoring suture is cut via ultrasonic blades at various angles.

EXAMPLE 2

Distal end of Surgipro™ suture is folded towards elongate body to create loop and glue is placed on elongate body and distal suture end is folded over and attached to elongate body, creating a fixed loop. Suture is then affixed to a cutting apparatus and anchoring suture is cut at various angles using a knife. Anchoring suture is then coated with a chemotherapeutic agent using solvent casting.

It should be noted that the present disclosure is not limited to wound closure and contemplates other procedures such as cosmetic and orthopedic procedures. Additionally, the above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A suture comprising:
an elongate body having a proximal portion and a distal portion and including one or more fibers, the proximal portion of the elongate body terminating in a free end and having a sufficient length for suturing a wound;
a loop disposed at the distal portion of the elongate body, the loop including a first segment including a first plurality of anchors disposed along a surface of the loop, the first plurality of anchors preventing movement of the loop through tissue in a proximal direction, and a second segment in which anchors are absent; and
a needle attached to the free end of the elongate body, wherein the elongate body further includes a second plurality of anchors preventing movement of the suture through tissue in the distal direction.

2. The suture according to claim 1, wherein the first plurality of anchors is adjacent to a transition area, the transition area defined by an intersection of the elongate body and the loop.

3. The suture according to claim 1, wherein the first plurality of anchors extend in a first direction and the second plurality of anchors extend in a second direction.

4. The suture according to claim 1, wherein the loop is formed by ultrasonic energy, welding, cutting, gluing, or molding.

5. The suture according to claim 4, wherein the loop is formed by ultrasonic energy and the proximal portion has the second plurality of anchors, the first plurality of anchors extending in a first direction and the second plurality of anchors extending in a second direction, the second direction being different from the first direction.

6. The suture according to claim 4, wherein the loop is created via use of an adhesive, glue, or a sealant.

7. The suture according to claim 1, wherein one or more of the anchors of either or both the first plurality of anchors and the second plurality of anchors defines at least one compound barb.

8. The suture according to claim 7, wherein the compound barb defines an inner surface having a first and second portion wherein the first portion includes a first orientation relative to a longitudinal axis of the elongate body, the second portion is disposed at a second orientation relative to the longitudinal axis, and optionally a third portion is disposed at a third orientation relative to the longitudinal axis, the first, second and third orientations being different.

9. The suture according to claim 1, wherein the medical device is absorbable, non-absorbable or combinations thereof.

10. The suture according to claim 9, wherein the medical device comprises an absorbable polymer selected from the group consisting of lactide, glycolide, caprolactone, valerolactone, trimethylene carbonate, 1,4-dioxanone, δ-valerolactone, ε-caprolactone, 1,4-dioxepan-2-one, 1,5-dioxepan-2-one, collagen, gut, polymer drugs, ethylene glycol, ethylene oxide, esteramides, γ-hydroxyvalerate, β-hydroxypropionate, alpha-hydroxy acid, and β-hydroxybuterate, collagen, cellulose, gut, and copolymers thereof.

11. The suture according to claim 9, wherein the suture comprises a non-absorbable polymer selected from the group consisting of silk, cotton, rubber, nylon, polypropylene, polyethylene, ultra high molecular weight polyethylene (UHMWPE), polyethylene terephthalate (PET), and polyesters and copolymers thereof.

12. The suture of claim 1, further comprising a medicinal agent.

13. A method of closing body tissue comprising:
providing a suture according to claim 1;
inserting the proximal portion of the medical device through a first section of tissue; and
advancing the proximal portion of the suture through a second section of tissue wherein the first plurality of anchors limits movement of the suture loop such that a segment of the loop remains outside a body tissue.

14. The method according to claim 13, further comprising:
inserting the proximal portion of the suture through the segment of the loop remaining outside the body tissue.

15. The suture according to claim 1, the loop further including a first branch and a second branch, wherein the first plurality of anchors is disposed on at least one of the first branch or the second branch.

16. The suture according to claim 15, further comprising a third plurality of anchors, wherein the third plurality of anchors is disposed on at least one of the first branch or the second branch.

17. The suture according to claim 1, wherein the elongate body is of sufficient length to be received through the loop.

18. The suture according to claim 1, wherein the loop is preformed.

19. The suture according to claim 1, wherein the proximal portion of the elongate body is configured to be received through the loop.

20. The suture according to claim 1, wherein the proximal portion of the elongate body is configured for repeatedly entering and exiting tissue until a wound site is closed.

21. The suture according to claim 1, wherein the second plurality of anchors is configured to prevent movement of the elongate body through tissue in a distal direction.

22. A suture comprising:
an elongate body formed from one or more fibers and having proximal and distal portions, the elongate body including a first plurality of anchors configured to prevent movement of the suture through tissue in the distal direction, the proximal portion having a sufficient length for suturing a wound; and
a loop disposed at the distal portion of the elongate body, the loop including a second plurality of anchors disposed along a surface of at least a portion of the loop configured to prevent movement of the loop through tissue in a proximal direction.

23. The suture according to claim 22, further including a needle attached to the proximal portion of the elongate body.

24. The suture according to claim 22, wherein the proximal portion of the elongate body is configured to be received through the loop.

25. The suture according to claim 22, wherein the first plurality of anchors is configured to prevent movement of the elongate body through tissue in a distal direction.

26. The suture according to claim 22, wherein the proximal portion is configured for repeatedly entering and exiting tissue until a wound site is closed.

27. A suture comprising:
an elongate suture body having a proximal portion and a distal portion and including one or more fibers, the proximal portion of the elongate body terminating in a free end and being configured for continuously entering and exiting tissue until a wound site is closed;
a loop disposed at the distal portion of the elongate body, the loop including a first segment including a first plurality of anchors disposed along a surface of the loop, the first plurality of anchors being configured to prevent movement of the loop through tissue in a proximal direction, and a second segment in which anchors are absent; and
a needle attached to the free end of the elongate body, wherein the elongate body further includes a second plurality of anchors configured to prevent movement of the elongate body through tissue in a distal direction.

* * * * *